(12) United States Patent
Ruggiero

(10) Patent No.: US 6,887,359 B2
(45) Date of Patent: May 3, 2005

(54) CHEMICAL MICRO-SENSOR

(75) Inventor: Anthony J. Ruggiero, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 426 days.

(21) Appl. No.: 09/877,961

(22) Filed: Jun. 8, 2001

(65) Prior Publication Data

US 2002/0189945 A1 Dec. 19, 2002

(51) Int. Cl.[7] .................. G01N 27/447; G01N 27/453; G01N 30/74

(52) U.S. Cl. ................ 204/452; 204/603; 73/23.4; 210/656; 95/82

(58) Field of Search ................ 204/450, 452, 204/600, 603; 73/19.02, 23.37, 23.4; 210/656; 95/82

(56) References Cited

U.S. PATENT DOCUMENTS

| | | | |
|---|---|---|---|
| 4,675,300 A | | 6/1987 | Zare et al. |
| 5,228,969 A | | 7/1993 | Hernandez |
| 6,005,663 A | | 12/1999 | Waterhouse et al. |
| 6,379,929 B1 | * | 4/2002 | Burns et al. ............ 435/91.2 |
| 6,381,025 B1 | * | 4/2002 | Bornhop et al. .......... 356/517 |

OTHER PUBLICATIONS

Krattiger et al, Anal. Chem. 1994, 66, pp. 1–8.*
Brandenburg, Sensors and Actuators B, 38–39 (1997), pp. 266–271.*
M. Yu, et al., "Attomole Amino Acid Determination by Capillary Zone Electrophoresis with Thermooptical Absorbance Detection," Jan. 1, 1989, Analytical Chemistry, vol. 61, No. 1, pp. 37–40.
M.S. Talary, et al., "Electromanipulation and Separation of Cells Using Travelling Electric Fields," Mar. 29, 1996, Institute of Molecular and Biomolecular Electronics, Univ. of Wales, pp. 2198–2203.
B. Krattiger, et al., "Hologram–Based Thermooptical Absorbance Detection in Capillary Electrophoresis: Separation of Nucleosides and Nucleotides," Anal. Chem. 1995, vol. 67, No. 1, pp. 124–130.
Z. Rosenzweig, et al., "Laser–Based Double–Beam Thermal Lens Detector for Microcolumn Liquid Chromatography," 1993, Applied Spectroscopy, vol. 47, pp. 1175–1179.

(Continued)

Primary Examiner—Kaj K. Olsen
(74) Attorney, Agent, or Firm—Eddie E. Scott; Alan H. Thompson

(57) ABSTRACT

An integrated optical capillary electrophoresis system for analyzing an analyte. A modulated optical pump beam impinges on an capillary containing the analyte/buffer solution which is separated by electrophoresis. The thermally-induced change in the index of refraction of light in said electrophoresis capillary is monitored using an integrated micro-interferometer. The interferometer includes a first interferometer arm intersecting the electrophoresis capillary proximate the excitation beam and a second, reference interferometer arm. Changes in index of refraction in the analyte measured by interrogating the interferometer state using white light interferometry and a phase-generated carrier demodulation technique. Background thermo-optical activity in the buffer solution is cancelled by splitting the pump beam and exciting pure buffer solution in a second section of capillary where it crosses the reference arm of the interferometer.

11 Claims, 7 Drawing Sheets

OTHER PUBLICATIONS

B. Seidel, et al., "Miniaturized Photothermal Sensors as Analytical Tools for Detection of Very Small Volumes in Chemical Process Control," 1997, Society of Photo–Optical Instrumentation Engineers, pp. 469–472.

D. Friedrich, "Optical–Phase–Shift Methods for Absorption Spectroscopy," 1983, Ultrasensitive Laser Spectroscopy, pp. 311–342.

C. Davis, et al., "Phase Fluctuation Optical Heterodyne Spectroscopy of Gases," Jul. 15, 1981, Applied Optics, vol. 20, No. 14, pp. 2539–2554 w/ Errata sheet, Dec. 15, 1981.

J. Stone, "Thermooptical Technique for the Measurement of Absorption Loss Spectrum in Liquids," Aug. 1973, Applied Optics, vol. 12, No. 8, pp. 1828–1830.

W. Faubel, et al., "Trace Analysis of Water Pollutants by Photothermal Phase Shift Spectroscopy with an Integrated Optical Microinterferometer," Dec. 1996, Society of Photo–Optical Instrumentation Engineers, pp. 3555–3560.

C. Davis, "Trace Detection in Gases Using Phase Fluctuation Optical Heterodyne Spectroscopy," Apr. 1, 1980, Appl. Phys. Lett. 36(7), pp. 515–518.

* cited by examiner

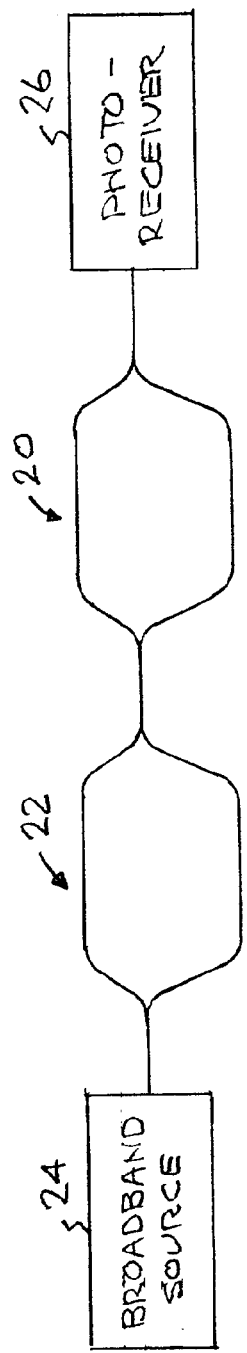
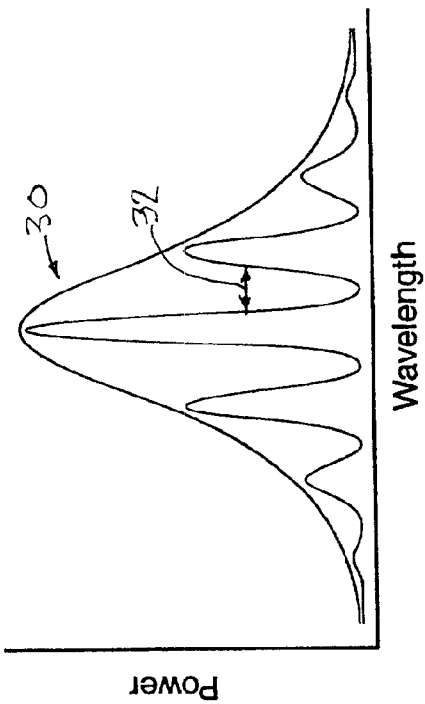
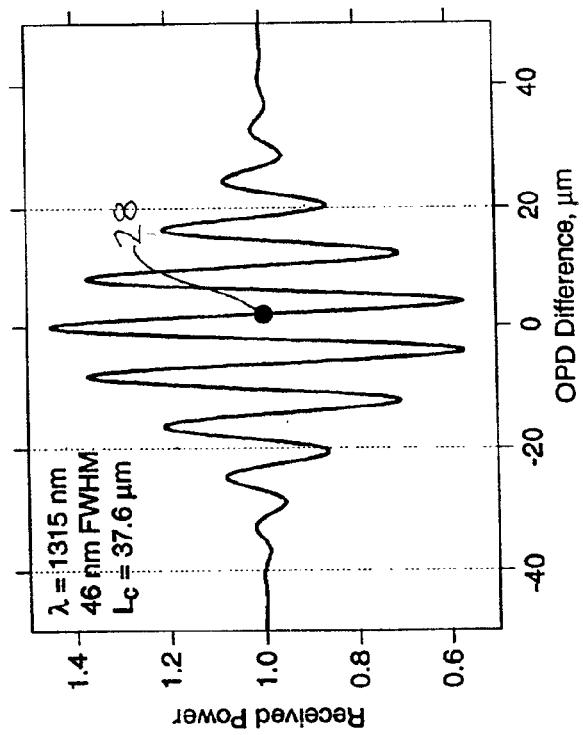
FIG. 3
FIG. 5
FIG. 4

CHEMICAL MICRO-SENSOR

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of Endeavor

The present invention relates to sensors and more particularly to a chemical micro-sensor.

2. State of Technology

U.S. Pat. No. 5,228,969 for a capillary electrophoresis apparatus including a capillary tube having an incorporated optical device, by Luis Hernandez, patented Jul. 20, 1993, provides the following description: "Capillary electrophoresis is a powerful separation technique making it possible to detect the presence of substances in detection zones of very small volume. This electrophoresis technique is particularly advantageous for application in the medical and biological field, with electrophoretic migration taking place either in a buffer or else on a gel."

U.S. Pat. No. 4,675,300 for a laser-excitation fluorescence detection electrokinetic separation, by Richard Zare and Ernst Gassmann, patented Jun. 23, 1987, provides the following description: "A fluoroassay method for detecting the presence of a target species in an electroosmotically pumpable fluorescible liquid sample which comprises: a.) placing said sample into one end of an electroosmotically pumpable-liquid-full narrow bore double open ended walled channel having a cross section dimension of not more than 500 μm and having at least a section which is translucent; b.) applying an effective electroosmotic pumping potential to said pumpable sample and pumpable liquid thereby transporting the sample through the channel; c.) irradiating the sample with coherent radiation of a wavelength effective to excite fluorescence in said sample; and d.) detecting a change in the fluorescence emitted through the translucent section of the channel as the target species moves past the translucent section."

U.S. Pat. No. 6,005,663 for an automated electrophoresis and fluorescence detection apparatus and method, by Waterhouse et al, patented Dec. 21, 1999, provides the following description: "Improved detection methods and apparatus which may be used individually or in combinations enhance the ability of the electrophoresis apparatus to detect fluorophore-labeled materials in short periods of time. One such apparatus comprises a housing adapted to receive an electrophoresis gel holder; an excitation source of electromagnetic radiation having a frequency effective to induce emission of electromagnetic radiation from the fluorophore; a plurality of optical fibers for delivering electromagnetic radiation from the excitation source to a linear array of excitation/detection sites on the gel holder, optical switching means for sequentially directing electromagnetic radiation into one of several pre-defined groups of the optical fibers; detection means such as a photomultiplier tube, or an array of photomultiplier tubes for detecting emission from the fluorophore induced by a radiation from the excitation source; and means for correlating a detected emission with the switching of the excitation electromagnetic radiation such that a given emission may be linked with the excitation/detection site being irradiated. For example, the optical switching means may alternate between directing radiation from the source into every other optical fiber, or may provide radiation in rotation to every third or fourth fiber. Alternatively, a spot array generation grating can be used for dividing an incident beam of coherent radiation into an array of excitation beamlets and directing each excitation beamlets to an excitation/detection site on the electrophoresis gel. Light emitting diode disposed to deliver excitation energy to an array of excitation/detection sites may also be used. This latter form of the apparatus is particularly advantageous due to the low costs of light emitting diodes (LEDs) compared to coherent light sources (e.g., lasers)."

The article, "Electromanipulation and Separation of Cells Using Traveling Electric Fields," by Talary M S, Burt J P H, Tame J A, and Pethig R, 1996, J. Phys. D: Appl. Phy. 29 219802203, provides the following description: "Apart from their use as particle separators, such micro-electrode devices are also envisaged to form integral components in the development of 'biofactory on a chip' technology."

SUMMARY OF THE INVENTION

Aspects of the invention include a microelectronic sensor system comprising a separation channel, an interferometer, a modulated excitation beam having a wavelength, a light source, and a photo receiver.

Further aspects of the invention include a sensor system, comprising a modulated laser excitation source, a separation capillary, ports in the separation capillary, electrodes in the ports, an interferometer having a first arm directed into the separation capillary and a second arm directed into the separation capillary, and an optical instrument that measures the interferometric state of the interferometer.

Another aspect of the invention includes an integrated sensor system device, comprising a separation capillary embedded inside of a solid material substrate such as glass, a laser excitation source, a chopping device to modulate the excitation source, a beam splitter that divides light from the chopped excitation source into at least two approximately equal beams, a buffer solution, an analyte dissolved in the buffer solution, a multiplicity of end ports into the capillary being respectively located at the two ends of and in the approximate center along the length of the capillary, with the analyte dissolved in a buffer solution being introduced into the capillary through the first of the end ports, and the buffer solution without analyte being introduced into the capillary through the second of the end ports and all of the fluids exiting through the center port, three electrodes deposited upon the substrate and immersed in the fluids in the ports, high-voltage direct-current power supplies interconnected between the electrodes, an interferometer formed from optical waveguides embedded inside of the solid material substrate, the interferometer having a first arm and a second arm, with the first arm operatively intersecting the separation capillary and the first beam of laser excitation source at a location between the first end port and the center port, and the second arm operatively intersecting the separation capillary and the second beam of laser excitation source at a location between the second end port and the center port, and an optical instrument that measures the interferometric state of the interferometer.

Another aspect of the invention includes a sensor system, comprising a separation capillary, a laser excitation source, a chopping device to modulate the excitation source, a beam splitter that divides light from the chopped excitation source into two approximately equal beams, a buffer solution, an analyte dissolved in the buffer solution, three ports into the capillary being respectively located at the two ends of and in the approximate center along the length of the capillary, with the analyte dissolved in a buffer solution being introduced into the capillary through the first of the end ports, and the buffer solution without analyte being introduced into the capillary through the second of the end ports, and all of the fluids exiting through the center port, three electrodes immersed in the fluids in the ports, several high-voltage direct-current power supplies interconnected between the electrodes, an interferometer, the interferometer having a first arm and a second arm, with the first arm operatively intersecting the separation capillary and the first beam of laser excitation source at a location between the first end port and the center port, and the second arm operatively intersecting the separation capillary and the second beam of laser excitation source at a location between the second end port and the center port, and an optical instrument that measures the interferometric state of the interferometer.

Another aspect of the invention includes a microanalytical method of analyzing an analyte, comprising the steps of delivering a modulated excitation beam to a separation channel having a first end port and an exit port, introducing an analyte into the first end port of the separation channel such that the analyte travels in the direction from the first end port to the exit port, measuring the change in the index of refraction of light versus time at a sample position located between the first end port and the exit port in the separation channel using an interferometer.

Another aspect of the invention includes a method of analyzing an analyte, comprising the steps of delivering a modulated excitation beam to a separation channel having a first end, a second end port and an exist port approximately in the center of the separation channel, wherein the excitation beam is split into two approximately equal optical excitation beams, wherein one of the optical excitation beams intersects the separation channel at a sample position located between the first end port and the exit port and the other optical excitation beam intersects the separation channel at a reference position located between the second end port and the exit port, introducing an analyte in a reference material into the first end port of the separation channel, such that the analyte travels in the direction from the first end port to the exit port, introducing pure reference material into the second end port of the separation channel, such that the reference material travels in the direction from the second end port to the exit port, measuring the change in the index of refraction of light versus time at a sample position between the first end port and the exit port in the separation channel and the change in the index of refraction of light versus time at a reference position between the second end port and the exit port in the separation channel using an interferometer with a first interferometer arm orthogonally intersecting the separation channel at the sample position and a second interferometer arm orthogonally intersecting the separation channel at the reference position, demodulating the time-varying index of refraction with a lock-in amplifier synchronized to the optical excitation beams, and recording the time history of the demodulated index of refraction.

BRIEF DESCRIPTION OF THE DRAWINGS

The accompanying drawings, which are incorporated into and form a part of the disclosure, illustrate embodiments of the invention, and, together with the description, serve to explain the principles of the invention.

FIG. 3 shows a diagramed basic WLI system.

FIG. 4 shows an autocorrelation plot.

FIG. 5 shows an interferogram.

DETAILED DESCRIPTION OF THE INVENTION

Figure 1A:
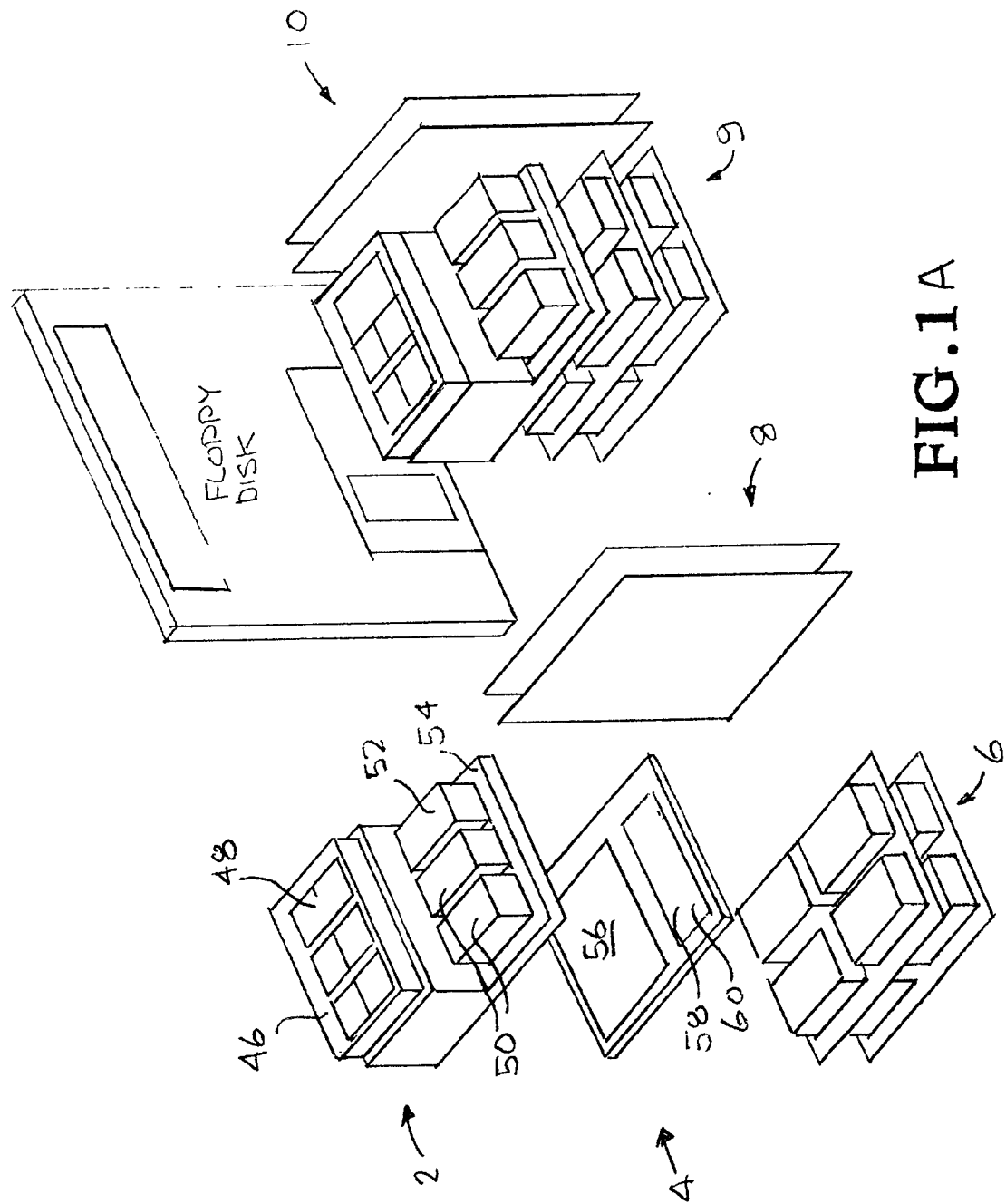
FIG. 1A is a conceptual diagram that illustrates an embodiment of a system constructed in accordance with the present invention.

Referring now to the drawings, specific embodiments of the invention are shown. The detailed description of the specific embodiments, together with the general description of the invention, serves to explain the principles of the invention. A conceptual diagram is shown that illustrates an embodiment of a system constructed in accordance with the present invention is shown in FIG. 1A. The system, designated generally by the reference numeral 10, provides a method and apparatus for sensing and analyzing chemical analytes and biologically active molecules. The system 10 may be used for sensing and analyzing chemical analytes and biologically active molecules in the field.

The system combines micro separation devices, microinterferometery, photonics, and microfluidics. An advantageous feature of the system is that raw samples collected in the field may be measured immediately upon collection. The system does not require sample fluorescence or chemical derivatisation with fluorescent labels. The sensor system has particular utility as a chemical micro-sensor that has detection sensitivities in the sub-ppm range. The sensor system provides a chemical microsensor system that is suitable for rapid, automated trace analysis and in-situ identification of aqueous effluents, extracts or condensates. Analyzing samples in situ keeps contamination to a minimum. The fundamental system architecture supports a variety of sampling and deployment options from simple fluid aspiration to unattended autonomous air sampling. The system is well suited to extremely high levels of integration and miniaturization.

The system 10 includes the following basic components: equipment for sample processing 2, a sensor chip 4, a power supply 6, a CPU and interfaces 8, and the remaining components 9 (discussed later). The sample processing equipment 2 includes a reagent cartridge 46, a waste reservoir 48, micro valves 50, a micro-pump 52, and a sample inlet 54. A reference inlet (not shown) can also be included. The sensor chip 4 includes integrated photonics 56, a sensor chip, e.g., capillary electrophoresis (CE) chip 58, and a micro laser 60. A 3-inch floppy disk is shown in FIG. 1A to illustrate the size of the components of system 10. The system may be economically mass-produced using a combination of integrated optical and planar chip micro-fabrication techniques. Some examples of integrated optical and planar chip micro-fabrication techniques are described and shown in the following journal article and patents which are incorporated herein by reference: J. Stone, J. Opt. Soc. Am. 62, 1828

(1972); C. C. Davis, Appl. Phys. Lett. 36, 515, (1980); C. C. Davis and S. J. Petuchowski, Appl. Optics 20, 2539 (1981); D. M. Friedrich "Optical Phase Shift Methods for Absoption Spectroscopy", Ch 3. *Ultrasensitive Laser Spectroscopy*, Ed. Kliger, Academic Press. New York (1983); W. Faubel, B. S. Seidel, and H. J. Ache, Opt. Eng. 35 (12) 3555 (1996); B. S. Seidel and W. Faubel, Opt. Eng. 36 (2) 469 (1997); Z. Rosenzweig and E. S. Yeung, Applied Spectroscopy 47, (8) 1175 (1993); M. Yu and N. Dovichi, Anal. Chem., 61,37 (1989); A. E. Bruno, A. Paulus, and D. J. Bornhop, Applied Spectroscopy 45, (8) 462 (1991); B. Krattiger, A. E. Bruno, H. M. Widmer, and R. Dandeliker, Anal. Chem., 67,124 (1989); U.S. Pat. No. 5,498,444 to J. D. Hayes titled, Method for Producing Micro-Optical Components; and U.S. Pat. No. 5,707,684 to J. D. Hayes and R. W. Cox, titled Method for Producing Micro-Optical Components.

Fluids stored in reagent cartridge 46 include sodium hydroxide for conditioning the CE capillaries within CE chip 58, buffer solution for prefilling the capillaries prior to analysis, water for cleaning and flushing, and/or any other reagents as required for a particular analysis protocol. Reagents are selected and directed into the capillaries through micro valves 50. The sample to be analyzed is collected by an external device not indicated, brought in through sample inlet 54, and is injected in the CE capillaries by micro pump 52. Waste fluids are returned to waste reservoir 48. All microfluidics components are interconnected on a common manifold.

CE chip 58 includes electrophoresis capillaries for analyte transport and analytical separation and an integrated interferometer for the measurement of changes in index of refraction in the analyte due to thermo-optical activity induced in the analyte by micro-laser 60. The state of the interferometer and hence the instantaneous index of refraction of the analyte is measured by the optical subsystem on the integrated photonics chip 56.

CPU and interface boards 8 are responsible for sequential actuation of all micro valves, pumps, lasers, and any other devices required in the various steps of an analysis cycle. The CPU also collects and analyzes measurements obtained from the interferometer to determine the constituency of the analyte.

Power supplies 6 provide low-voltage direct current for all electronic subsystems and components, and high-voltage direct current for the purpose of inducing electro-osmotic flow in the CE capillaries.

General Concept of Operation of an Embodiment

Figure 1B:
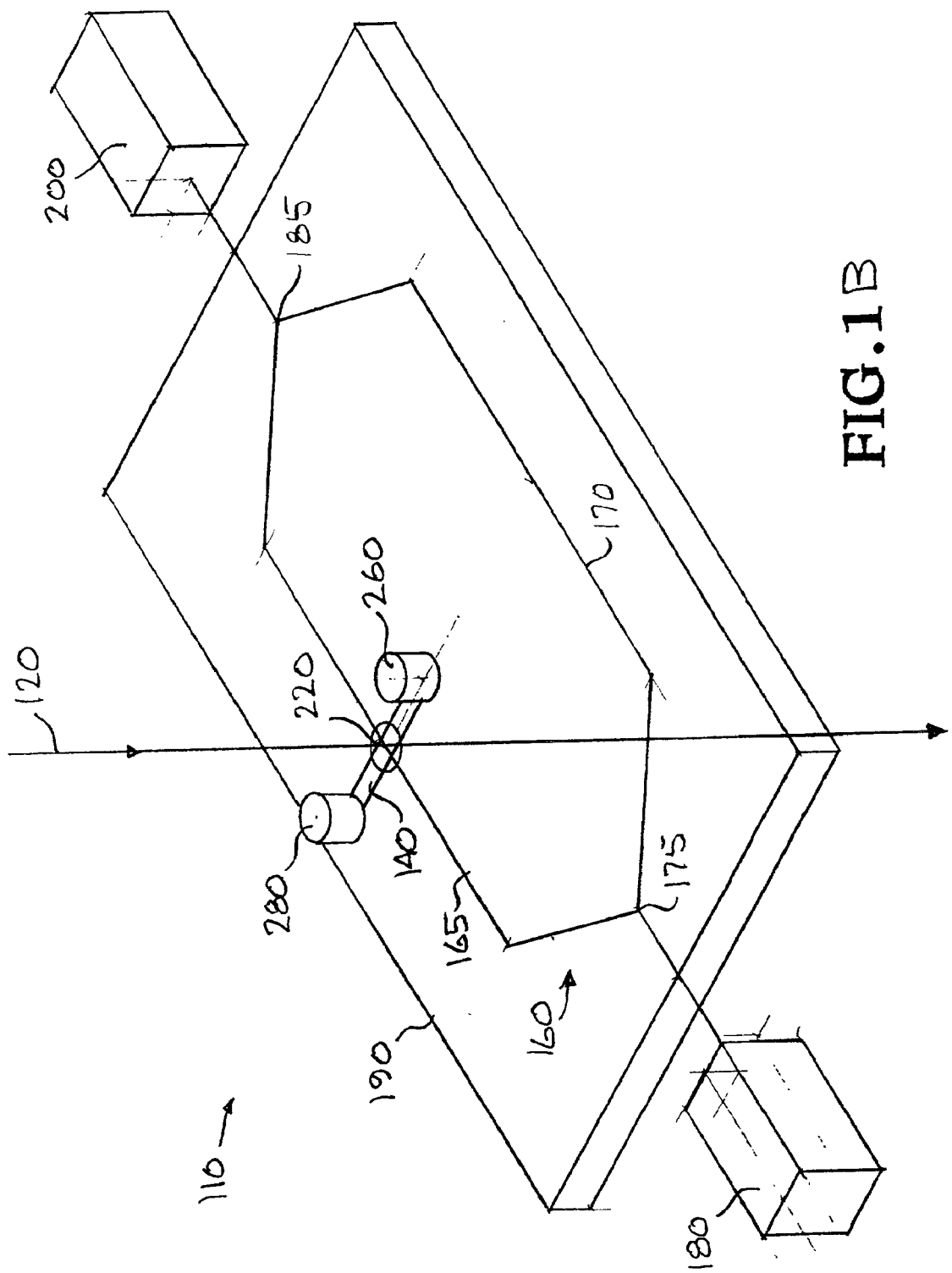
FIG. 1B illustrates the general concept of operation of an embodiment of a system constructed in accordance with the present invention

Referring now to FIG. 1B, the general concept of operation of an embodiment of a system constructed in accordance with the present invention is shown. The system, generally designated by the reference numeral 110, includes a modulated excitation beam 120, a separation channel, such as a capillary electrophoresis (CE) separation capillary 140 that transports analytes in a reference material, e.g., a buffer solution, and a micro-interferometer 160. Micro-interferometer 160 and CE capillary 140 are constructed on a common substrate comprising a single integrated chip 190.

The micro-interferometer 160 is fabricated from waveguides embedded in the substrate of CE chip 190 and is comprised of two arms, a sample arm 165 and a reference arm 170. The micro-interferometer 160 is interrogated by a laser 180 and a photoreceiver 200. Any change in the optical path difference (OPD) between the two arms of the micro-interferometer is detected as a change in fringe intensity at the photoreceiver. Micro-interferometer 160 and CE capillary 140 intersect one another orthogonally within the substrate in such a way that light travelling in the micro-interferometer passes through the solution flowing in the capillary. The modulated excitation beam 120 pass passes through the CE capillary 140 at position 220 normal to the surface of the chip 190.

In one embodiment, the reference material is a buffer solution. A sample reservoir 280 containing analytes in buffer solution and a waste reservoir 260 are attached to the CE capillary 140 to provide a means for moving the analytes through the CE capillary 140 such that the analytes pass through position 220.

When modulated excitation beam 120 interacts with said analytes in buffer solution, the temperature of said solution changes in phase with the modulation. This change in temperature results in a proportional change in index of refraction of the solution. Said changes in index of refraction are easily detected as changes in optical path difference (OPD) of the micro-interferometer 160. This overall process is known as thermo-optic interferometry. The magnitude of the index change is proportional to the analyte concentration, the excitation beam intensity, and the absorption cross-section of the analyte at the wavelength of excitation. With calibration, concentration measurements are quantitative and highly repeatable.

In another embodiment (not shown), the reference material is a carrier gas, e.g., helium, or a carrier liquid, e.g., methylene chloride. In such an embodiment, the separation channel is a chromatography column. Use of a chromatography column in place of the CE capillary accommodates separation methods such as gas chromatography (GC), high pressure liquid chromatography (HPLC), or size exclusion chromatography (SEC). Such an embodiment has an injection port as opposed to a sample reservoir. The analytes are contained in a carrier gas or carrier liquid as opposed to a buffer solution. An exhaust or waste port is attached to the center of the chromatography column to provide a means for moving the analytes through the chromatography column such that the analytes pass through at a position on the column equivalent to position 220 on the CE capillary. The column comprises an optically transmissive viewing port at this position, such as glass or quartz, whereas the remainder of the column can be any material (opaque or transmissive), e.g., stainless steel.

Pump Laser with Background Subtraction

Figure 2A:
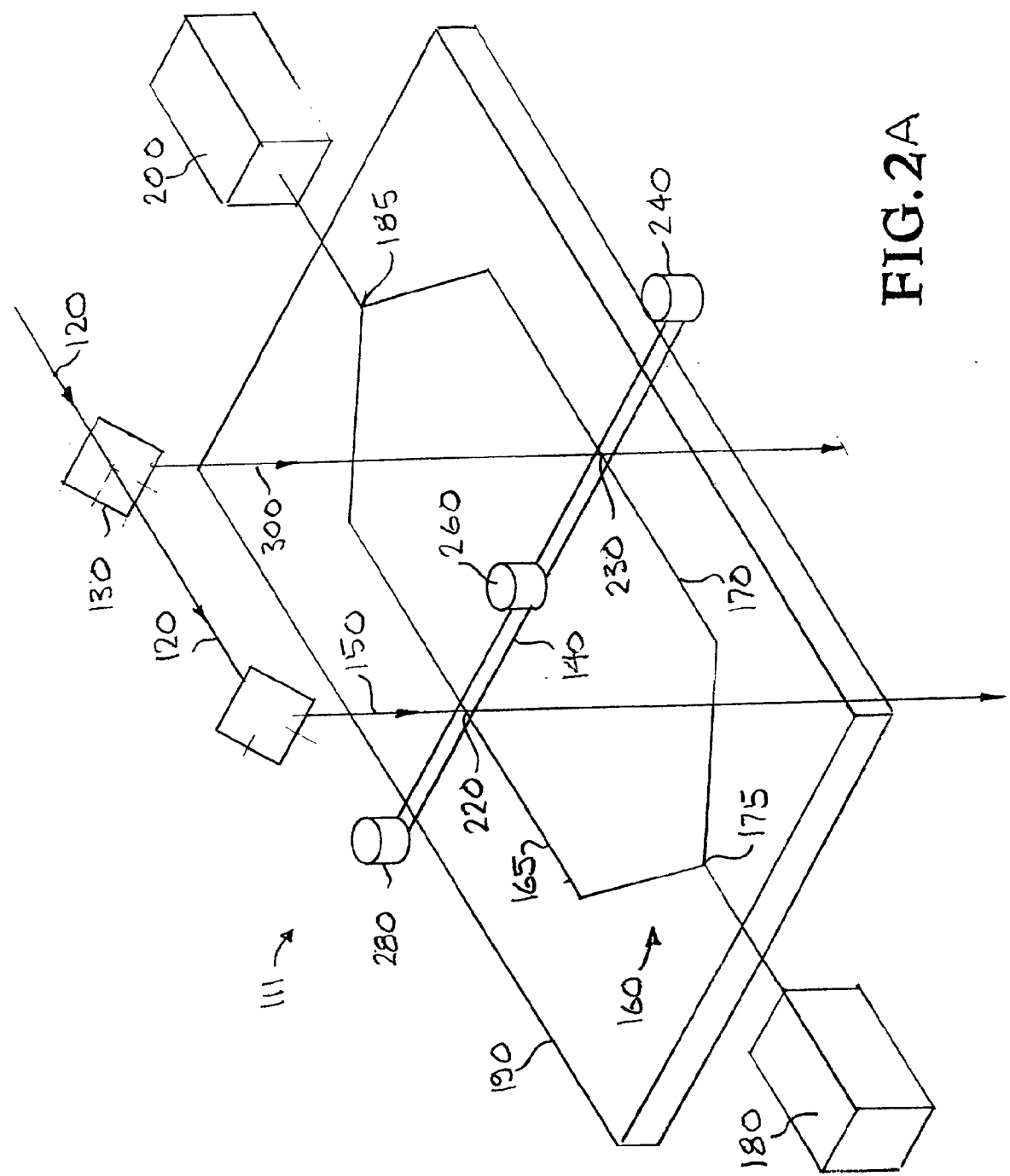
FIG. 2A illustrates the general concept of operation of an embodiment of a system constructed in accordance with the present invention.

The general concept of operation of an embodiment of a system constructed in accordance with the present invention is shown in FIG. 2A. The system, generally designated by the reference numeral 111, includes a modulated excitation beam 120, a separation channel, e.g., a capillary electrophoresis (CE) separation capillary 140 that transports either analytes in a buffer solution or a buffer solution, and a micro-interferometer 160. Micro-interferometer 160 and CE capillary 140 are constructed on a common substrate comprising a single integrated chip 190.

Referring to FIG. 2A, an embodiment of an optical detection portion of an integrated optical capillary electrophoresis (IOCE) chemical sensor comprises the following components: a modulated excitation beam 120, a capillary electrophoresis (CE) separation capillary 140 that transports either analytes in a reference material or only reference material, and a micro-interferometer 160 which includes a laser 180 and a photoreceiver 200. In this embodiment the reference material is a liquid buffer solution. Positions 220 and 230 represent areas of said CE capillary where an optical phase of light from modulated excitation beam 120 passing through said CE capillary is modified by a change in absorption induced by a refractive index change in the liquid (analyte and buffer or buffer) that is present in said CE capillary. A sample reservoir 280 containing analytes and buffer solution, a waste reservoir 260, and a buffer reservoir 240 are attached to said CE capillary to provide a means for moving said analytes through said CE capillary such that said analytes pass through position 220 and said buffer solution which is free of said analytes passes through position 230.

The micro-interferometer 160 is fabricated from waveguides embedded in the substrate of CE chip 190 and is comprised of two arms, a sample arm 165 and a reference arm 170 and two couplers 175 and 185. Micro-interferometer 160 is interrogated by a laser 180 and a photoreceiver 200. Any change in the optical path difference (OPD) between the two arms of the micro-interferometer is detected as a change in fringe intensity at the photoreceiver.

The modulated excitation beam 120 passes through beam-splitter 130, producing two nearly equal excitation beams 150 and 300. Beam 150 passes through the CE capillary 140 in position 220 while beam 300 passes through the CE capillary 140 in position 230.

A sample reservoir 280 containing analytes and buffer solution, a waste reservoir 260, and a buffer reservoir 240 are attached to the CE capillary 140 to provide a means for moving the analytes through the CE capillary 140 such that the analytes pass through position 220 and said buffer solution which is free of said analytes passes through position 230.

When modulated excitation beam 300 interacts with said buffer solution or modulated excitation beam 150 interacts with said analytes in buffer solution, the temperature of said solutions changes in phase with the modulation. This change in temperature results in a proportional change in index of refraction of the fluid. Said changes in index of refraction are easily detected as changes in OPD of the micro-interferometer 160.

Thermo-optical activity is induced by a pump laser that is directed normal to the surface of the IOCE chip at the intersection of the separation channel, e.g., CE capillary 140 and the interferometer, shown in FIG. 2A as positions 220 and 230. Two beams are supplied: one at a signal intersection where the analyte/buffer solution passes 220, and the other at a background intersection 230 where only pure buffer solution passes. Signals from the two interferometer arms, sample arm 165 and reference arm 170 are inherently out of phase. Therefore, if the fluids at the two intersections are identical and the pump beams are matched, the signals will cancel, leaving zero background phase shift in the received signal. This permits a first-order cancellation of background thermo-optical signals due to absorption in the buffer solution.

The embodiment of this invention as described above and shown in FIG. 2A represents a solution to a known problem with thermo-optical sensing regarding undesired sensitivity to the buffer solution. Regardless of the choice of fluid for the buffer solution, some thermo-optical response will always be present and will be sensed as a change in index of refraction in that solution. The dual-point excitation method described here nearly cancels the system's response to the buffer solution but does not affect the response to the analyte, thereby greatly increasing the signal-to-noise ratio.

Figure 2B:
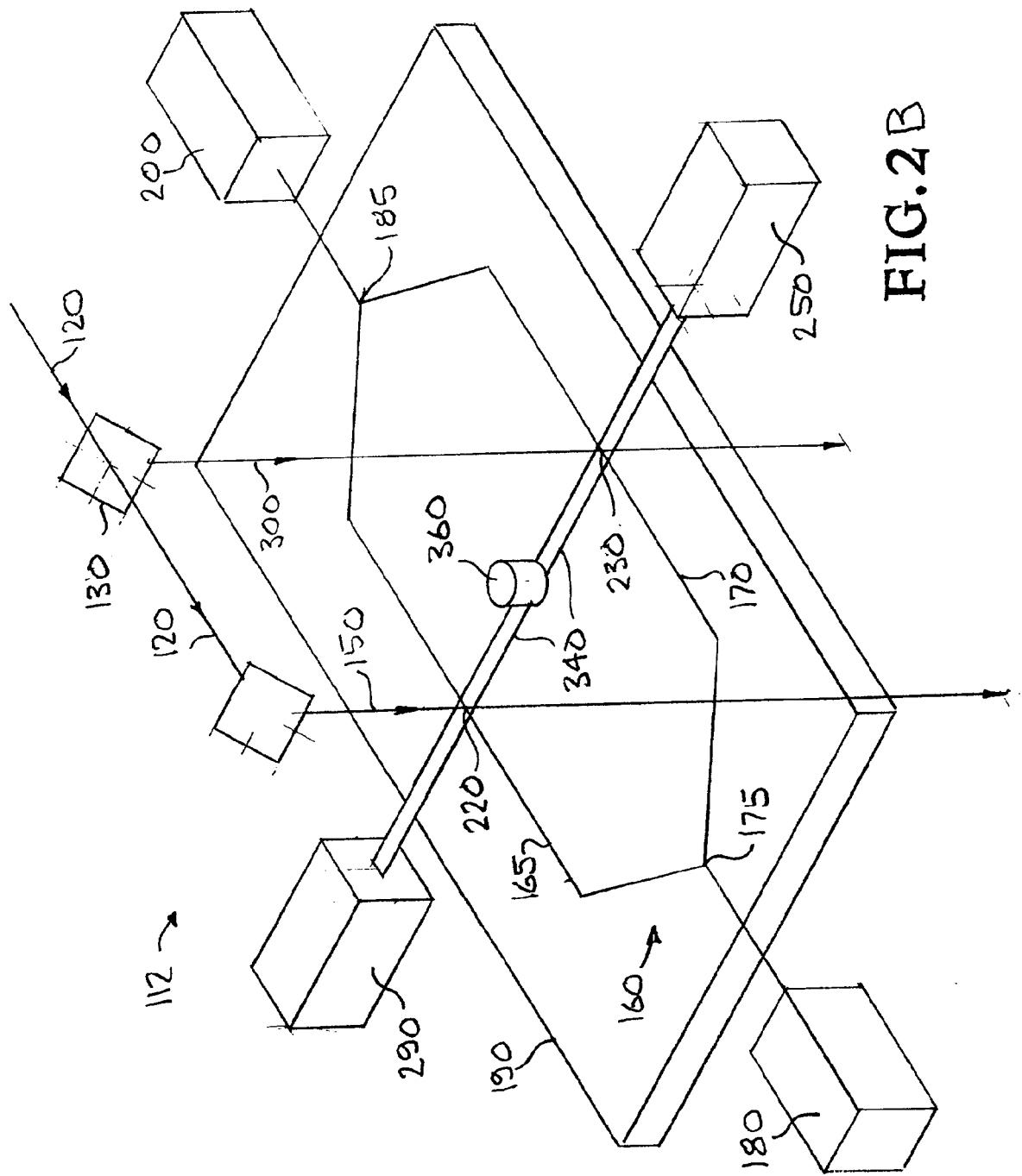
FIG. 2B illustrates the general concept of operation of an embodiment of a system constructed in accordance with the present invention.

The general concept of operation of an embodiment of an optical portion of an integrated optical gas chromatography (IOGC) chemical sensor shown in FIG. 2B and generally designated by the reference numeral 112 is the same as that described for the embodiment of the optical portion of an IOCE chemical sensor shown in FIG. 2A and described above. The system includes a modulated excitation beam 120, a separation channel, e.g., a gas chromotagraphy (GC) separation column 340 that transports either analytes in a carrier gas or only a carrier gas, and a micro-interferometer 160. Micro-interferometer 160 and GC column 340 are constructed on a common substrate comprising a single integrated chip 190.

Referring to FIG. 2B, an embodiment of an optical detection portion of an integrated optical gas chromatography chemical sensor comprises the following components: a modulated excitation beam 120, a gas chromatography (GC) separation column 340 that transports either analytes in a reference material or only a reference material, and a micro-interferometer 160 which includes a laser 180 and a photoreceiver 200. In this embodiment the reference material is a carrier gas, such as helium. Positions 220 and 230 represent areas of said GC column that are made of an optically transmissive material where an optical phase of light from modulated excitation beam 120 passing through said GC column is modified by a change in absorption induced by a refractive index change in the gas (analyte and carrier gas or carrier gas) that is present in said GC column. A sample injection port 290 containing analytes and carrier gas, a waste or exhaust port 360, and a carrier injection port 250 are attached to GC column 340 to provide a means for moving said analytes through said GC column such that said analytes pass through position 220 and said carrier gas which is free of said analytes passes through position 230.

The micro-interferometer 160 fabricated from waveguides embedded in the substrate of CE chip 190 and is comprised of two arms, a sample arm 165 and a reference arm 170 and two couplers 175 and 185. The micro-interferometer 160 is interrogated by a laser 180 and a photoreceiver 200. Any change in the optical path difference (OPD) between the two arms of the micro-interferometer is detected as a change in fringe intensity at the photoreceiver.

The modulated excitation beam 120 passes through beam-splitter 130, producing two nearly equal excitation beams 150 and 300. Beam 150 passes through the GC column in position 220 while beam 300 passes through the GC column in position 230.

A sample injection port 290 containing analytes and carrier gas, a waste reservoir 360, and a reference injection port 250 are attached to the GC column 340 to provide a means for moving the analytes through GC column 340 such that the analytes pass through position 220 and said carrier gas which is free of said analytes passes through position 230.

When modulated excitation beam 300 interacts with said carrier gas or modulated excitation beam 150 interacts with said analytes in the carrier gas, the temperature of said gases changes in phase with the modulation. This change in temperature results in a proportional change in index of refraction of the gas. Said changes in index of refraction are easily detected as changes in OPD of the micro-interferometer 160.

Thermo-optical activity is induced by a pump laser that is directed normal to the surface of the IOGC chip at the intersection of the separation channel, e.g., GC column 340, and the interferometer, shown in FIG. 2B as positions 220 and 230. The gas channel is optically transmissive at positions 220 and 230, however, the rest of the GC column may be made of an opaque material. Two beams are supplied: one at a signal intersection where the analyte/carrier gas passes 220, and the other at a background intersection 230 where only pure carrier gas passes. Signals from the two interferometer arms, sample arm 165 and reference arm 170 are inherently out of phase. Therefore, if the gases at the two intersections are identical and the pump beams are matched, the signals will cancel, leaving zero background phase shift in the received signal. This permits a first-order cancellation of background thermo-optical signals due to absorption in the carrier gas.

The embodiment of this invention as described above and shown in FIG. 2B represents a solution to a known problem with thermo-optical sensing regarding undesired sensitivity to the carrier gas. Regardless of the choice of carrier gas, some thermo-optical response will always be present and will be sensed as a change in index of refraction in that gas. The dual-point excitation method described here nearly cancels the system's response to the carrier gas but does not affect the response to the analyte, thereby greatly increasing the signal-to-noise ratio.

Separating Complex Analyte Mixtures

The system may separate and identify components of complex mixtures using capillary electrophoresis, separating said components based on their charge-to-mass ratio and/or other micro-chromatographic parameters using this integrated optical capillary electrophoresis (IOCE) microsensor. Other embodiments of the system may incorporate other separation techniques such as gas chromatography, size exclusion chromatography, or high pressure liquid chromatography.

In the interferometric sensor of the system, the optical phase of the light passing through the arms of the interferometer is modulated by a change in thermo-optically induced refractive index in the CE capillary caused by the chemical species to be detected. The phase modulation is then measured interferometrically by comparing the phase of the light in the CE sample arm to the reference arm. Optical phase information is demodulated, by detection of the intensity of all the light emerging from the interferometer rather than a spatially selected component or fringe. Consequently, the signal is independent of thermal lensing artifacts due to the spatial distribution of the excitation beam and is also much less sensitive to misalignment than conventional fringe shift techniques. The system is also well suited to both active and passive homodyne stabilization techniques that would be required for field deployment. Other advantages include, wide dynamic range, high sensitivity, low overall energy budget and the potential for device multiplexing for decreased analysis time and/or improved species identification.

The wavelength of the modulated optical excitation source is selected to match the analyte absorption spectra and is delivered to the electrophoresis capillary. The choice of wavelength may add an additional dimension of selectivity to the analysis. As an example, if the analyte of interest absorbs favorably at a unique visible wavelength while all expected background substances absorb only in the ultraviolet, a great deal of background rejection is possible.

Interrogating the Micro-Interferometer

There are several embodiments of the invention with regards to interrogating the state of the micro-interferometer and thus measuring the instantaneous index of refraction of analytes present within the separation capillary. In the first embodiment, the interferometer may be monitored with a narrow line diode laser operating at 1310 nm. In such a system, the interferometer is set to a dark fringe using an integrated waveguide modulator in one arm of the interferometer. The diode laser light is detected with a photodetector and a lock-in amplifier synchronized to the modulation frequency of the excitation source. The micro-interferometer signal is monitored to measure the analyte transit time through the capillary after electro-kinetic sample injection.

The transit time when calibrated provides a signature for the analyte. Another embodiment uses a waveguide modulator to modulate the interferometer output so that a phase generated carrier technique may be implemented to remove interferometer noise and fading effects. Another embodiment involves white light interferometery. Another embodiment involves white light interferometery combined with a phase-generated carrier technique.

White Light Interferometry (WLI) System

In the interest of reducing cost and complexity, the system that uses a conventional coherent light interferometry with a narrow-band laser source to observe fringe shifts in the integrated interferometer may be converted to white light interferometry (WLI) using an incoherent or broadband source. WLI, or low-coherence interferometry, may be an important technique in remote measurement of parameters such as displacement, temperature, pressure, and refractive index. Some advantages of WLI in the IOCE application include:

1. Optical power fluctuations that occur along interconnecting fibers do not compromise measurement accuracy.
2. Very short optical path differences (OPDs) may be used in the interferometers, in contrast to the long OPDs required in conventional fiber interferometry.
3. A low-cost super luminescent diode (SLD) may be used as a source.
4. An expensive optical isolator may be eliminated and packaging may be simplified because SLDs are insensitive to back reflections.
5. Wavelength stability in the laser is unimportant. Therefore, neither ultra-stable temperature controls nor exceptionally stable power supplies are required.

A basic WLI system is diagrammed in FIG. 3. Two optical path differences (OPDs) are arranged in series and are referred to as the receiving interferometer (RI) 20 and the sensing interferometer (SI) 22. OPDs of each interferometer are arranged to be several times the coherence length of a source 24, which guarantees that fringes are not visible if either OPD is illuminated individually. To obtain interference at an output 26 of RI 20, the OPDs of the two interferometers must match within the coherence length of source 24.

The transfer function of this two-interferometer system is the output resulting from the sum of the electric fields arising light traversing the four possible paths through the system. At the entrance and exit of each interferometer, the split ratio may vary from 50/50; these values are represented by $K_1$. The expression for the received power when driven by a low-coherence source is an autocorrelation function:

$$I = I_0 \{1 + 2\sqrt{K_1 K_2 K_3 K_4}\; e^{\left(\frac{-2\Delta X}{L_c}\right)^2} \cos(\kappa \Delta X) \} \quad (1)$$

where $I_0$ is the incident laser power, $L_c$ is the source central wavenumber for the source, and X is the difference in OPD between the two interferometers.

A solution for this equation is represented graphically in FIG. 4 using the SLD source specifications from the IOCE system. For the purpose of observing small changes in OPD due to thermo-optically induced changes in index, the system response is optimized by statically tuning the OPD difference to a quadrature point 28 marked with a dot in FIG. 4. Quadrature point 28 represents the position where the slope is greatest and the maximal signal will be obtained.

An intuitive view of WLI is obtained by looking at interferograms measured with an optical spectrum analyzer (OSA). If a single interferometer is excited with a broadband source, the interferogram of FIG. 5 is seen. The overall shape 30 is that of the spectrum of the source, while the individual peak spacing 32 is defined in frequency space. When two interferometers with identical OPDs are placed in series, their interferograms match and the result is unchanged. But if the OPDs are mismatched, i.e., not identical, the peaks no longer align and some cancellation occurs, distorting the output interferogram and reducing the total output power. Thus, a change in OPD of one of the interferometers causes a change in power, corresponding to the variations seen in the autocorrelation plot of FIG. 4, above.

Locating the central fringe in WLI may be challenging because the broadband source does not provide a large intensity difference between adjacent fringes. For the IOCE application, the accuracy of the photolithography processes used in interferometer fabrication guarantees the OPD match. When initially adjusting the system, it is possible to observe the output power while trimming one OPD (via a phase modulator, described later). By sweeping through power minima and maxima, an optimal quadrature point may be located. By contrast, several techniques which do not utilize photolithography processes have been developed for use in non-integrated systems, including the use of fiber interferometers and bulk optical interferometers. All require two sources at different wavelengths adding complexity to the method.

WLI System Description

Figure 6:
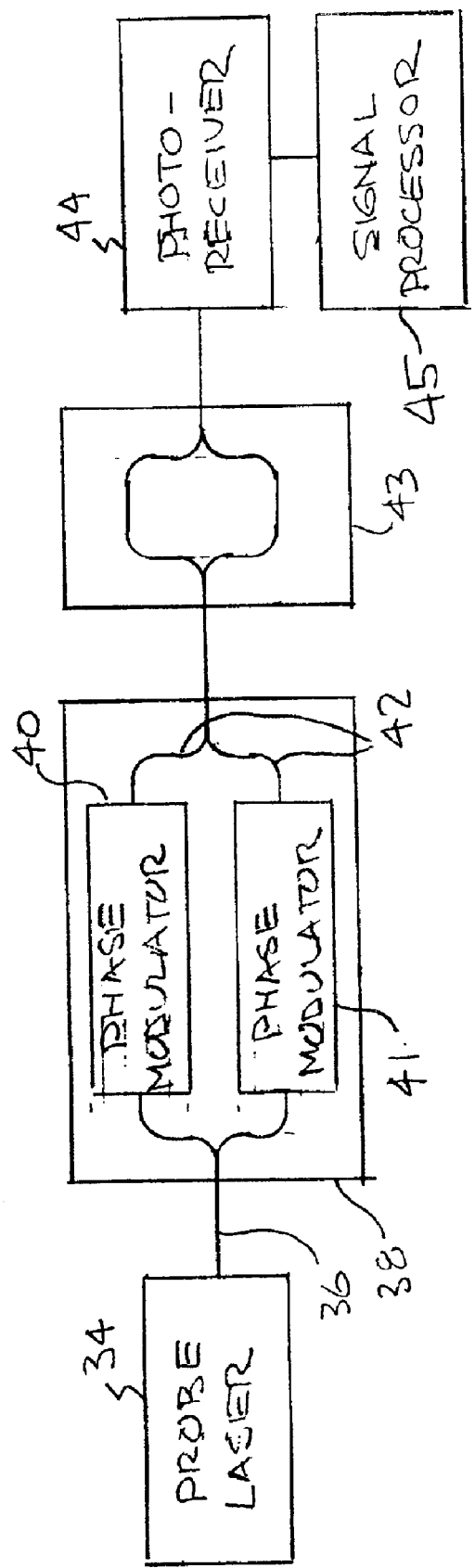
FIG. 6 is a schematic illustration of an embodiment of an IOCE interferometry system.

An embodiment of an IOCE interferometry system is shown schematically in FIG. 6. A probe laser 34, such as an Anritsu AS3B381PX superluminescent diode (SLD) may supply 1 mW continuous wave (CW) at a center wavelength of 1315 nm with a full-width, half-maximum (FWHM) of 46 nm. Polarization-maintaining fiber 36 may be used to couple all components. Light from SLD 34 feeds a custom-designed application-specific integrated optical circuit generically 38, such as, a Bookham ASOC, that contains a pair of phase modulators 40, 41 and a Mach-Zehnder interferometer (MZI) 42 with an OPD of 588 μm plus or minus about 1.5 μm. An effective embodiment of the device uses mismatched modulators; one (40) is capable of producing a phase shift of 200° while the other (41) achieves 500° at a current of 100 mA. The latter, wide-range channel, may be used for high-frequency modulation (discussed later), and the limited-range channel may be used as a steady-state OPD trim. Effective response of the wide-range leg is 75 mRad/mA. The IOCE chip 43 has an OPD of 586±20 μm, nearly matching the Bookham device 38. A perfect OPD match may be achieved by adjusting modulator 40 with a variable DC current. The photoreceiver 44 is a New Focus model 2011 with low noise, adjustable gain, and a bandwidth >100 kHz. The output of photoreceiver 44 feeds a signal processor 45 that measures variations in the received optical power in response to changes in OPD.

Interferometric Signal Processing

A very sensitive interferometric measurement technique with sub-fringe resolution and wide dynamic range is a preferred technique for IOCE application. An interrogation and demodulation technique that involves a phase generated carrier (PGC) interrogation followed by a digital demodulation scheme may be used. The nonlinear interrogation signals are processed into a signal which is linear with optical phase. This direct measurement of optical phase is then proportional to index of refraction as scaled by the wavelength and the path length. It is also independent of optical intensity.

The PGC technique requires that a dynamic phase modulation (dither) be placed upon the interferometer. To accomplish this, a phase modulator may be inserted in the reference (upstream) interferometer and then driven with a sinusoidal carrier. Received intensity at the output of the measuring (downstream) interferometer is then demodulated. While such demodulation may be accomplished by analog circuit techniques, a digital approach has been commercially implemented by Optiphase Inc. (Van Nuys, Calif.). An Optiphase model OPD-250 digital demodulator board used in the present invention may yield an analog dynamic range of $10^6$.

Traditionally, the PGC technique has provided excellent performance only with coherent light interferometry. However, the implementation of PGC with WLI in the present invention has demonstrated low-noise, high-stability performance equal to that observed with coherent light. The use of integrated photonics, particularly in the area of integrated phase modulators and integrated interferometers, drastically reduces noise and drift due to vibration and differential temperature. Thus, the present invention benefits from the combined advantages of both PGC and WLI techniques.

Excitation Laser

Referring to FIG. 1B, an embodiment of a sensor system may use an argon ion laser as the pump laser, for instance, either a Liconix Model 5304A providing 488 nm CW light or a Lexel Model 95 SHG with intra-cavity doubling providing 244 nm CW light. The beam may be chopped by an EG & G Model 650 optical chopper at approximately 1 kHz. This modulation appears on the output of the PGC demodulator for later detection by a lock-in amplifier. The visible beam may be attenuated as required, coupled into single-mode fiber, and then split 50/50 in a fiber splitter. UV light may be transmitted via table-mounted optics and a 50/50 beamsplitter. Light out of each fiber may be coupled via aspheric lens pairs and directed at the underside of the CE chip at the required intersections. Nominal power at the chip is 50 mW at 488 nm and 5 mW at 244 nm in each leg. Differential power adjustment between legs (to optimize background subtraction) may be accomplished by slight defocusing or repositioning of the beams.

Electronic Systems

Figure 7:
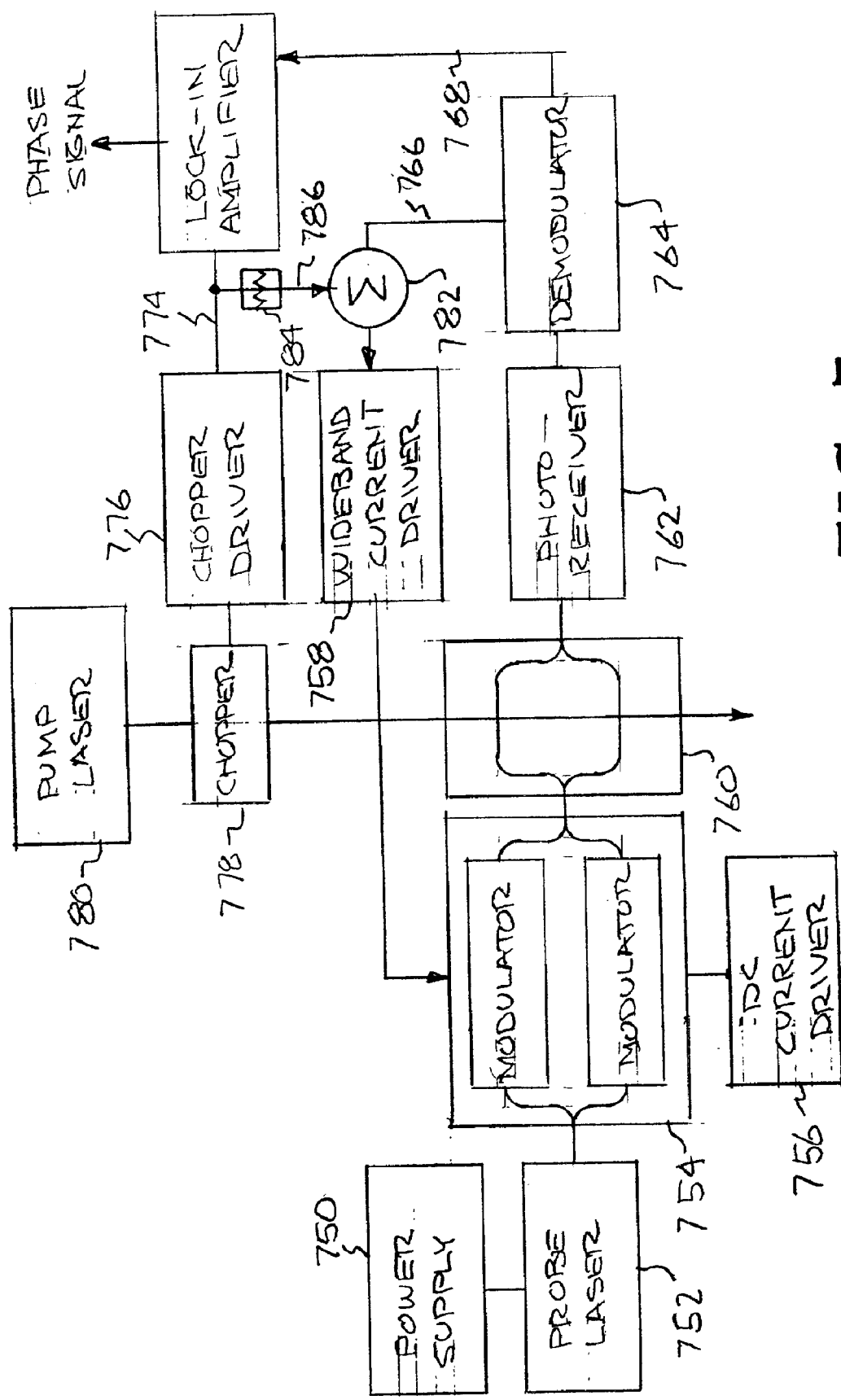
FIG. 7 is a flow diagram of an embodiment of the complete electro-optical portion of the IOCE system.

FIG. 7 is a flow diagram of an embodiment of the complete electro-optical portion of the IOCE system. The system shown in FIG. 7 includes all features required to support the embodiment of white light interferometry with phase-generated carrier (PGC) demodulation as described above. A probe laser 752 is powered by a constant-current power supplies, such as those from Wavelength Electronics, Bozeman, MT. Two phase modulators, incorporated into the photonic integrated circuit 754, are driven by constant-current power supplies. One of said power supplies, 756, generates an unmodulated DC current and is used to adjust the OPD of the Mach-Zehnder interferometer included on photonic integrated circuit 754. Power supply 758 delivers a constant current modulated at a high frequency that represent the carrier in the PGC method.

Light from probe laser 754 passes through integrated integrated optical (photonics) circuit 754 and then through the CE chip 760 and finally into photoreceiver 762, which may be a New Focus (Santa Clara, Calif.) model 2011. The electrical signal from photoreceiver 762 is demodulated by PGC demodulator 764, which may be an Optiphase, Inc. (Van Nuys, Calif.) model OPD-250. PGC demodulator 764 provides a high-frequency carrier 766 which may be at 95 kHz. Carrier 766 is fed to a summation amplifier 782, the output of which modulates power supply 758. The other output of PGC demodulator 764 is the demodulated output 768 which feeds the signal input of lock-in amplifier 770 which may be a Femto Messtechnik GmbH (Berlin, Germany) model LIA-BV-150. Said lock-in amplifier demodulates the output of said PGC demodulator 764 and produces an output signal 772 that is proportional to the absolute phase state of the micro-interferometer located on CE chip 760. A second output of lock-in amplifier 770 is a reference frequency signal 774 that may operate at 1 kHz. The primary destination of said reference frequency signal is a chopper driver 776 which may be an EG & G Model 650. Said chopper driver is thereby synchronized and phase-locked with said reference frequency. Said chopper driver drives chopper 778 which modulates the excitation light from laser 780. Said modulated excitation light provides energy to analyte solutions flowing in CE chip 760.

The second destination for reference frequency signal 774 is potentiometer 784 which allows adjustment of the amplitude of said signal. The output of potentiometer 784 is calibration signal 786. Said calibration signal is fed to summing amplifier 782, when desired by the operator, to provide a 1 kHz modulation of known amplitude. This simplifies system testing and calibration by providing a simulated thermo-optical response which may be detected by the entire electro-optical system as if it were a real thermo-optical response due to the presence of an analyte.

Additional Analyte Discrimination Methods

An embodiment of the invention includes an additional feature when analyzing biologically active molecules and/or cells, i.e., traveling wave dielectrophoresis (TWD). Dielectrophoresis separates particles based on the fact that when placed in an AC electric field, polarized particles experience a translational force depending on the applied field frequency. In the case of a bio-particle, the induced polarizability depends on the surface charge and conductance, the membrane capacitance and conductance, the cytoplasmic conductance and the properties of the internal cell/particle components and organelles. The applied field frequency therefore may be used to provide a signature for a given dielectric particle.

An additional force vector may be induced by the AC TWD effect to the forces being applied to the molecules via capillary electrophoreses. Thus, said molecules and/or cells may be characterized on the basis of dielectric properties, as well as charge to mass ratio and shape within the IOCE sensor architecture allowing three parameters to be used in the classification and detection process, i.e., AC frequency, CE transit time, and the excitation wavelength used for said thermo-optic detection.

Several separation capillaries may be combined onto one chip referred to as multiplexing which allows for the detection of numerous types of analytes and biologically active species simultaneously.

Applications of the Invention

The sensor system embodiment of the invention described above has applications in environmental monitoring, forensics science, pharmacological and medical sample analysis, industrial chemical process monitoring, military and civilian protection against weapons and chemical and biological agents, treaty verification efforts, prevention of terrorist threats, and tactical force protection. For example, the present invention has applications for the rapid, automated trace chemical analysis and in-situ identification of aqueous effluents, extracts or condensates associated with the development, production or handling of weapons of mass destruction (WMD) and the battlefield and civilian detection of biological and chemical warfare agents (CBW). Identification, detection and monitoring of chemical and biological warfare agents and precursors are crucial to treaty verification efforts, prevention of terrorist threats, and tactical force protection. Real time field sensors developed for these applications must be capable of detecting target compounds in unpredictable and chemically complex environments with sufficient dynamic range to handle both trace and overload conditions.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A microelectronic sensor system comprising:

at least one separation channel, at least one interferometer, said interferometer including an arm and an integrated chip, wherein said separation channel and said interferometer arm orthogonally intersect each other at least once on said integrated chip, at least one modulated excitation beam having a wavelength, at least one light source, at least one photo receiver, a lock-in amplifier, a probe laser, a polarization-maintaining fiber used to couple all components, an integrated optical circuit having two phase modulators and a Mach-Zehnder interferometer.

2. The microelectronic sensor system of claim 1, wherein said probe laser is a superluminescent diode supplying 1 mW continuous wave at a center wavelength of 1315 nm with a full-width, half-maximum of 46 nm, said Mach-Zehnder interferometer has an optical path distance between about 585.5 $\mu$m and about 589.5 $\mu$m, one of said phase modulators produces a phase shift of about 200° at a current of 100 mA, and the other of said phase modulators produces a phase shift of about 500 at a current of about 100 mA.

3. A microelectronic sensor system comprising:

at least one separation channel, at least one interferometer, said interferometer including an arm and an integrated chip, wherein said separation channel and said interferometer arm orthogonally intersect each other at least once on said integrated chip, at least one modulated excitation beam having a wavelength, at least one light source, and at least one photo receiver, and wherein said interferometer has a sample arm and a reference arm, said separation channel has a first end port, a second end port and an exit port located approximately in the center of the separation channel, wherein said sample arm orthogonally intersects said separation channel at a sample position located between said first end port and said exit port and said reference arm orthogonally intersects said separation channel at a reference position located between said second end port and said exit port.

4. The microelectronic sensor system of claim 3, further comprising:
a beamsplitter, wherein said beamsplitter divides light from said modulated excitation beam into at least two approximately equal beams, producing a first excitation beam and a second excitation beam, wherein said first excitation beam passes through said separation channel at said sample position and said second excitation beam passes through said separation channel at said reference position.

5. An integrated sensor system device, comprising:
a separation capillary embedded inside of a solid material substrate such as glass,
a laser excitation source,
a chopping device to modulate said excitation source,
a beam splitter that divides light from said chopped excitation source into at least two approximately equal beams,
a buffer solution,
an analyte dissolved in said buffer solution,
a multiplicity of end ports into said capillary being respectively located at the two ends of and in the approximate center along the length of said capillary, with said analyte dissolved in a buffer solution being introduced into said capillary through the first of said end ports, and said buffer solution without analyte being introduced into said capillary through the second of said end ports and all of said fluids exiting through said center port,
three electrodes deposited upon said substrate and immersed in said fluids in said ports,
high-voltage direct-current power supplies interconnected between said electrodes,
an interferometer comprising an integrated chip formed from optical waveguides embedded inside of said solid material substrate, said interferometer having a first arm and a second arm, with said first arm operatively intersecting said separation capillary and said first beam of laser excitation source at a location between said first end port and said center port, and said second arm operatively intersecting said separation capillary and said second beam of laser excitation source at a location between said second end port and said center port, and
an optical instrument that measures the interferometric state of said interferometer.

6. A sensor system, comprising:
a separation capillary,
a laser excitation source,
a chopping device to modulate said excitation source,
a beam splitter that divides light from said chopped excitation source into two approximately equal beams,
a buffer solution,
an analyte dissolved in said buffer solution,
three ports into said capillary being respectively located at the two ends of and in the approximate center along the length of said capillary, with said analyte dissolved in a buffer solution being introduced into said capillary through the first of said end ports, and said buffer solution without analyte being introduced into said capillary through the second of said end ports, and all of said fluids exiting through said center port,
three electrodes immersed in said fluids in said ports,
several high-voltage direct-current power supplies interconnected between said electrodes,
an interferometer comprising an integrated chip, said interferometer having a first arm and a second arm, with said first arm operatively intersecting said separation capillary and said first beam of laser excitation source at a location between said first end port and said center port, and said second arm operatively intersecting said separation capillary and said second beam of laser excitation source at a location between said second end port and said center port, and
an optical instrument that measures the interferometric state of said interferometer.

7. A micro-analytical method of analyzing an analyte, comprising the steps of:
providing an interferometer that comprises an integrated chip, said interferometer having an interferometer arm position over a separation channel, wherein said separation channel and said interferometer arm orthogonally intersect each other at least once on said integrated chip,
delivering a modulated excitation beam to a separation channel having a first end port and an exit port,
introducing an analyte into the first end port of said separation channel such that the analyte travels in the direction from said first end port to said exit port,
measuring the change in the index of refraction of light versus time at a sample position located between said first end port and said exit port in the separation channel using an interferometer, and
further comprising dissolving said analyte in a reference material before introduction into said separation channel,
introducing a reference material into a second end port of said separation channel, such that the reference material travels in the direction from said second end port to said exit port creating a time-varying index of refraction along said separation channel, and
measuring the change in the index of refraction of light versus time at a reference position between said second end port and said exit port in the separation channel using an interferometer.

8. A micro-analytical method of analyzing an analyte, comprising the steps of:
providing an interferometer that comprises an integrated chip, said interferometer having an interferometer arm position over a separation channel, wherein said separation channel and said interferometer arm orthogonally intersect each other at least once on said integrated chip,
delivering a modulated excitation beam to a separation channel having a first end port and an exit port,
introducing an analyte into the first end port of said separation channel such that the analyte travels in the direction from said first end port to said exit port,
measuring the change in the index of refraction of light versus time at a sample position located between said first end port and said exit port in the separation channel using an interferometer, and
further comprising vaporizing said analyte in a carrier gas before introduction into said separation channel,
introducing said carrier gas into a second end port of said separation channel,
such that the carrier gas travels in the direction from said second end port to said exit port creating a time-varying index of refraction along said separation channel, measuring the change in the index of refraction of light versus time at a reference position between said second end port and said exit port in the separation channel using an interferometer.

9. A method of analyzing an analyte, comprising the steps of:

providing an interferometer that comprises an integrated chip, said interferometer having an interferometer arm position over a separation channel, wherein said separation channel and said interferometer arm orthogonally intersect each other at least once on said integrated chip, delivering a modulated excitation beam to said separation channel having a first end, a second end port and an exit port approximately in the center of said separation channel, wherein said excitation beam is split into two approximately equal optical excitation beams, wherein one of said optical excitation beams intersects the separation channel at a sample position located between said first end port and said exit port and the other optical excitation beam intersects the separation channel at a reference position located between said second end port and said exit port, introducing an analyte in a reference material into said first end port of the separation channel, such that the analyte travels in the direction from said first end port to said exit port, introducing pure reference material into said second end port of the separation channel, such that the reference material travels in the direction from said second end port to said exit port, measuring the change in the index of refraction of light versus time at a sample position between said first end port and said exit port in the separation channel and the change in the index of refraction of light versus time at a reference position between said second end port and said exit port in the separation channel using an interferometer with a first interferometer arm orthogonally intersecting the separation channel at said sample position and a second interferometer arm orthogonally intersecting the separation channel at said reference position, demodulating said time-varying index of refraction with a lock-in amplifier synchronized to said optical excitation beams, and recording the time history of said demodulated index of refraction.

10. The method of claim 9, further comprising the step of:

measuring the transit time of said analyte through said separation channel by observing the time of arrival of said time history data thus providing a temporal signature for the analyte.

11. The method of claim 10, wherein said separation channel is an electrophoresis capillary, further comprising the step of:

applying high voltage to said separation channel thus causing said analyte and reference material to flow toward and out of the exit port by electro-osmotic flow and with electrophoretic separation occurring.

* * * * *